United States Patent
Forestiere et al.

(10) Patent No.: US 8,748,671 B2
(45) Date of Patent: Jun. 10, 2014

(54) ETHER PRODUCTION METHOD INVOLVING ALCOHOL SEPARATION BY AN IONIC LIQUID

(75) Inventors: Alain Forestiere, Vernaison (FR); Renaud Cadours, Francheville (FR); Christophe Vallee, Sassenage (FR)

(73) Assignee: IFP Energies Nouvelles, Rueil-Malmaison Cedex (FR)

( * ) Notice: Subject to any disclaimer, the term of this patent is extended or adjusted under 35 U.S.C. 154(b) by 1612 days.

(21) Appl. No.: 12/300,007

(22) PCT Filed: Apr. 30, 2007

(86) PCT No.: PCT/FR2007/000745
§ 371 (c)(1),
(2), (4) Date: Oct. 4, 2010

(87) PCT Pub. No.: WO2007/128912
PCT Pub. Date: Nov. 15, 2007

(65) Prior Publication Data
US 2011/0021847 A1    Jan. 27, 2011

(30) Foreign Application Priority Data
May 9, 2006 (FR) ...................................... 06 04174

(51) Int. Cl.
*C07C 41/06* (2006.01)
*C07C 41/34* (2006.01)

(52) U.S. Cl.
CPC ...................................... *C07C 41/34* (2013.01)
USPC ........................................... 568/697; 568/699

(58) Field of Classification Search
CPC .................................................... C07C 41/06
USPC .................................................. 568/697, 699
See application file for complete search history.

(56) References Cited

U.S. PATENT DOCUMENTS

| | | | |
|---|---|---|---|
| 5,329,051 A * | 7/1994 | Eason et al. | ................... 568/699 |
| 5,348,624 A | 9/1994 | Pucci et al. | |

FOREIGN PATENT DOCUMENTS

| | | |
|---|---|---|
| EP | 0542596 A1 | 5/1993 |
| EP | 0755911 A1 | 1/1997 |

OTHER PUBLICATIONS

Letcher et al. (Fluid Phase Equilibria, vol. 219, May 2004, pp. 107-112).*
Arce, Alberto et al. "Purification of Ethyl tert-Butyl Ether from its Mixtures with Ethanol by using an Ionic Liquid." Chemical Engineering Journal 115 (2006): 219-223.
Arce, Alberto et al. "tert-Amyl Ethyl Ether Separation from its Mixtures with Ethanol Using the 1-Butyl-3-methylimidazolium Trifluoromethanesulfonate Ionic Liquid: Liquid—Liquid Equilibrium." Ind. Eng. Chem. Res. 43 (2004): 8323-8327.

* cited by examiner

*Primary Examiner* — Rosalynd Keys
(74) *Attorney, Agent, or Firm* — Millen, White, Zelano & Branigan, P.C.

(57) ABSTRACT

An enhanced method of producing ethers from iso-olefins and alcohols comprises at least one stage of separation of the excess alcohol by an ionic liquid. The ether-hydrocarbon-alcohol effluent treated in said separation stage by the ionic liquid comes from the reaction section and/or from a fractionating column. The separated and condensed alcohol is recycled in the process.

20 Claims, 2 Drawing Sheets

ETHER PRODUCTION METHOD INVOLVING ALCOHOL SEPARATION BY AN IONIC LIQUID

FIELD OF THE INVENTION

Figure 1:
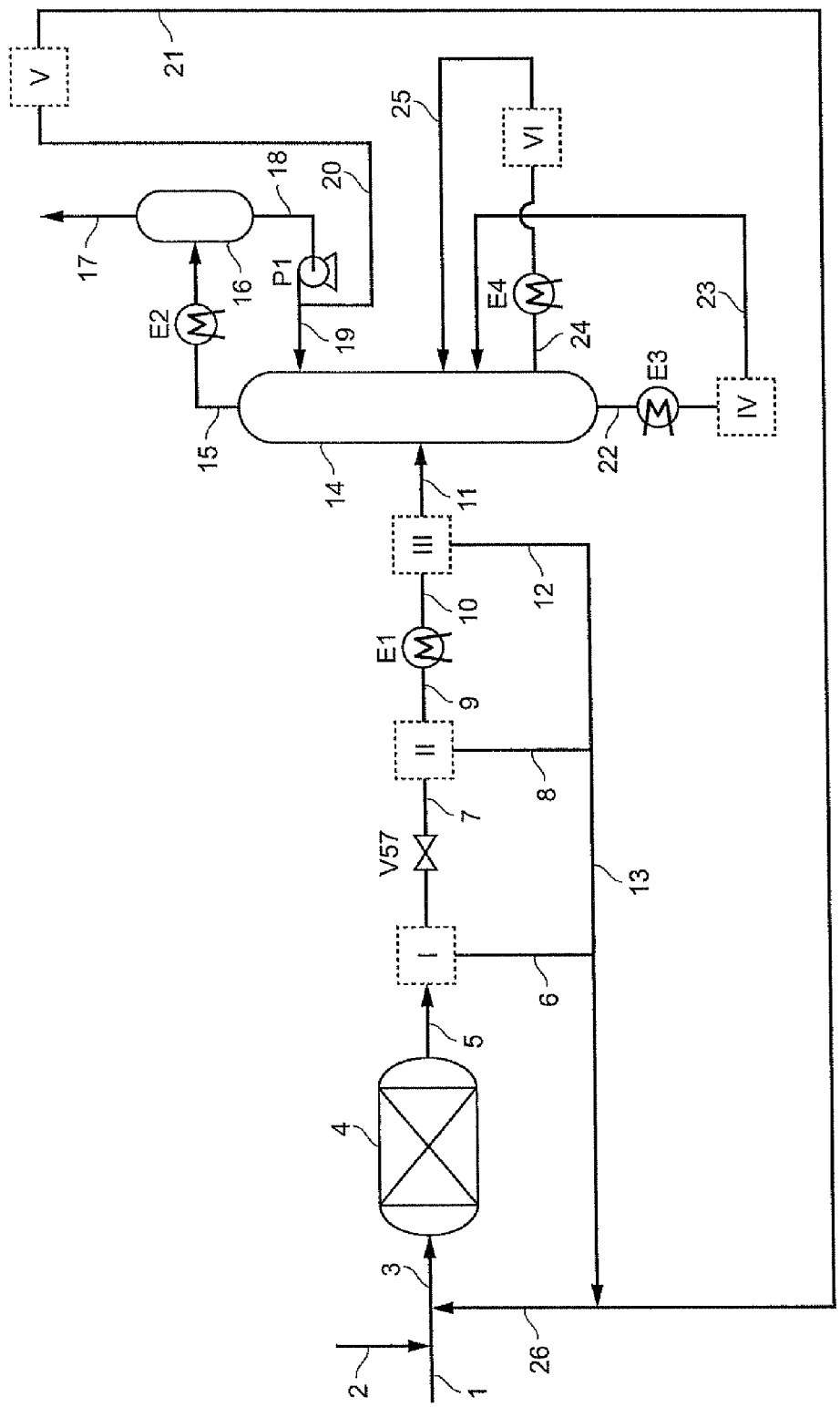

The invention relates to methods for producing ethers from alcohols and olefins, and more particularly purification and separation by an ionic liquid of the excess alcohol to be recycled in the process.

BACKGROUND OF THE INVENTION

Fuel ether production methods conventionally consist in adding an alcohol to a branched olefin. Examples thereof are the methyl tertiobutyl ether (MTBE) production processes wherein methanol is added to isobutene, ethyl tertiobutyl ether (ETBE) production processes by addition of ethanol to isobutene, as well as processes for producing various ethers such as isopropyl tertiobutyl ether (IPTBE) from isopropanol and isobutene, tertio amyl methyl ether (TAME) from methanol and isoamylene, or ethyl tertioamyl ether (ETAE) from ethanol and isoamylene.

In general terms, all these processes comprise a first reaction section wherein the ether is produced in the liquid phase, at low temperature, by reaction of an iso-olefin with a monoalcohol, in the presence of an acid catalyst, generally of sulfonic polystyrene type in acid form. The reaction is carried out in one or more reactors in series. The reaction is very selective towards the iso-olefins but it is always carried out with excess alcohol so as to cause the chemical ether formation equilibrium to shift. The feed treated is generally a hydrocarbon cut derived from FCC, steam cracking or from a dehydrogenation operation, and it generally contains less than 50 wt. % iso-olefins, the rest consisting of a mixture of hydrocarbons practically inert towards the etherification reaction.

The main reaction section is then followed by a separation stage whose goal is to separate the ether fraction formed, the unreactive or unreacted hydrocarbons for later use, and the excess alcohol. This alcohol is generally recycled to the main reaction section.

The separation section generally consists of a fractionating column that possibly comprises an additional catalytic section intended to push the conversion of the iso-olefins to form ether in larger amounts. It generally allows to collect the ether at the bottom and the hydrocarbon mixture at the top of the column. Division of the alcohol among these two fractions occurs according to the nature of the alcohol and to the composition of the hydrocarbon cut used, and therefore finally according to the nature of the ether produced in the reaction section.

Operation of the fractionating column is generally complex because, in principle, one wants to benefit from the existence of azeotropes between alcohol and ether, alcohol and hydrocarbons, in order to optimize the separation and/or the separation/reaction in a reactive distillation column when the goal is to maximize the production of ether, as described for example in patent applications FR-2,675,055 A1 and FR-2,678,846 A1.

Patent FR-2,683,523 aims to wash the alcohol-ether cut obtained at the bottom of the fractionating column with water. In addition to the difficulty linked with the recovery of the alcohol through a sequence of columns, the technique is penalized by the production, on the one hand, of a water-saturated ether requiring later treatment and, on the other hand, of a water-laden alcohol.

When the alcohol is not methanol, since for the latter there is no azeotrope formation, various methods of recovering the alcohol contained in the ether in the bottom of the separation section have already been proposed.

Patent FR-2,672,048 provides an alternative to patent FR-2,683,523 by taking advantage of the variation, with the pressure, of the composition of the azeotrope of the alcohol-ether mixture. Using two distillation columns operating at two different pressures allows to obtain the ether in the bottom of the first column operated at high pressure and the alcohol in the bottom of the second column operated at low pressure. Using an azeotrope-generating agent in order to facilitate separation of the ether and of the alcohol according to the latter technique is described in patent FR-2,673,624. This technique has the drawback of being investment costly and of recycling with the alcohol various impurities present in the ether cut from the synthesis stage. Recycling these impurities leads to their progressive accumulation that may eventually disturb the proper operation of the process.

Patent FR-2,719,581 aims to achieve separation of the various compounds from the reaction section by distillation, with a first column supplied with the alcohol-ether-hydrocarbon mixture allowing to recover the hydrocarbons at the top of the column and the purified ether at the bottom of the column, and a second column supplied by lateral withdrawal from the first column, for which the alcohol is collected in the bottom and an alcohol-ether-hydrocarbon mixture is collected at the top and recycled to the first column.

The different techniques presented above have in common the fact that they produce at the top of the first distillation column an alcohol-rich hydrocarbon cut. The solution that is generally selected for collecting this alcohol consists in washing this hydrocarbon cut with water. The first drawback thereof is that a water-saturated hydrocarbon cut is obtained, the second one is that it requires using a distillation column for the water-alcohol mixture thus obtained. This distillation is furthermore generally penalized by the formation of an azeotrope between the alcohol and the water.

In the case of methanol that forms no azeotrope with water, various alcohol recovery methods are provided, but the drawback then lies in the methanol concentration of the liquid water-methanol effluent obtained. Separation of the water and of the methanol can be carried out by distillation, but this technique is generally energy costly, or by stripping with a water-saturated gas as described in patents EP-362,023 and EP-783,031. The latter technique however has limits in terms of recoverable methanol amount.

Consequently, except for methanol, the various techniques presented above lead to recycle to the reaction section a highly water-laden alcohol. In general, the water content can be up to 10% by weight in the case of ethanol, up to 30% by weight in the case of a C3 alcohol and 45% by weight in the case of a C5 alcohol. When the highly water-laden alcohol is recycled to the reaction section, deactivation of the resins is observed through decrease of their acidity, as well as the formation of unwanted alcohols resulting from the addition of water to the branched olefins instead of the desired reaction consisting in the addition of these alcohols to the branched olefins.

An alternative to the extraction of alcohol by water consists in using a non-aqueous ionic liquid. Arce et al. (Ind. Eng. Chem. Res. 2004, 43, 8323) have assessed this solution for extracting the ethanol contained in tert-amyl ethyl ether (TAEE) by 1-butyl-3-methylimidazolium trifluoromethanesulfonate. The results obtained imply the possibility of extracting the alcohol contained in the ether, but at the cost of a high co-absorption of ether in the extraction solvent. The lack of selectivity of the ionic liquid selected does not favour an economical use of this extraction solvent.

Besides, Arce et al. (Chemical Engineering Journal 115 (2006) 219-223) have also investigated the possibility of using this solvent for extracting the ethanol contained in ETBE. According to Arce et al., the ionic liquid is therefore used to separate the alcohol from the ether produced.

SUMMARY OF THE INVENTION

The present invention provides an enhanced method of producing ethers from iso-olefins and alcohols, comprising the following stages:

a) mixing a hydrocarbon fraction containing iso-olefins with at least one alcohol stream, b) etherification reaction by reaction of the mixture obtained in stage a) in the presence of an ion-exchange resin so as to obtain an ether-hydrocarbon-alcohol effluent, c) separation, in a fractionating column, of said ether-hydrocarbon-alcohol effluent into a first ether-enriched effluent containing part of the excess alcohol and into a second hydrocarbon-enriched effluent containing the other part of the excess alcohol, and at least one of the effluents obtained in stages b) and c) is treated by carrying out the following stages:

d) contacting said effluent(s) with a non-aqueous ionic liquid so that the ionic liquid becomes laden with alcohol and the effluent becomes depleted in alcohol, the ionic liquid having the general formula $Q^+A^-$, $Q^+$ designating an ammonium, phosphonium and/or sulfonium cation, and $A^-$ designating an anion likely to form a liquid salt with said cation, e) regenerating the alcohol-laden ionic liquid by separating said ionic liquid and the alcohol, said separation consisting in evaporating the alcohol, then in condensing it, and wherein said separated and condensed alcohol is recycled in the process.

Advantageously, the method according to the invention allows to recycle an alcohol whose purity level and low water content favour the etherification reaction in terms of selectivity and activity of the etherification catalyst. For example, the alcohol content, in the case of the production of ETBE and therefore of use of ethanol, is limited to less than 0.5% by weight in the ether produced, whereas the conventional scheme of the prior art leads to an alcohol content above 2.5% by weight.

DETAILED DESCRIPTION

The various stages of the method according to the invention are described hereafter in detail.

Stage a)

The feed of the ether production method can consist of any mixture of hydrocarbons containing iso-olefins and of an alcohol source.

The hydrocarbon used is generally the isobutene of a C4 cut from isobutane steam cracking or catalytic cracking or dehydrogenation, or from tertiobutanol dehydration. It is also possible to use the isopentenes of a C5 cut from naphtha steam cracking or catalytic cracking, or any other cut containing branched olefins.

The alcohol source preferably is methanol or ethanol, but it can also be selected from among other oxygen-containing compounds such as propanol, isopropanol, n-butanols, 2-methylpropanol or glycerol.

The common commercial quality depends on the type of alcohol used. For example, for methanol, the minimum purity is 99.85% by weight and the maximum water content is 0.1% by weight. For agriculturally-derived ethanol, still by way of example, the minimum purity is 99.7% by weight and the water content is 0.3% by weight maximum.

The alcohol flowing into the reaction section comes either from an outer source or from recycling the alcohol after stage e). The proportion of recycled alcohol in relation to the total amount entering the reaction section generally ranges between 1 and 20% by volume, preferably between 1 and 8% by volume.

Stage b)

The etherification reaction is carried out in the liquid phase in the presence of an ion-exchange resin of macroreticulated sulfonic type and with excess alcohol so as to shift the equilibrium to the production of ether. Industrially, the excess alcohol can reach 10% by mole.

The reaction section is made up of at least one reactor, and when two or more reactors are present, a finishing reactor can be optionally used. The main reactor operates at a temperature generally ranging between 50° C. and 90° C., and the finishing reactor operates at a lower temperature of the order of 50° C.

Although the operating conditions slightly depend on the reaction type, according to the ether produced (MTBE or ETBE for example), they are in the following ranges:

alcohol/iso-olefin molar ratio: 0.8 to 1.3, preferably 0.9-1.2 temperature of the first reactor: 40° C. to 100° C., preferably 50° C.-90° C.

temperature of the finishing reactor: 30° C. to 80° C., preferably 40° C.-60° C.

The pressure is selected and adjusted by the person skilled in the art so as to avoid any vaporization in the reactor. It generally ranges between 0.5 and 2.0 MPa.

Stage c)

Separation of the ether fraction formed from the ether-hydrocarbon-alcohol fraction from the reaction section is generally carried out in a fractionating column allowing to predominantly recover, at the bottom, the ether and, at the top, predominantly the hydrocarbon fraction. The fractionating column is generally a conventional distillation column or a reactive distillation column replacing, if need be, a finishing reactor and the fractionating column.

Stage d)

At the end of stage b) and/or c), one or more alcohol-laden liquid effluents are treated by contacting the effluent with a non-aqueous ionic liquid so that the ionic liquid becomes laden with alcohol and the effluent is depleted in alcohol, the ionic liquid having the general formula $Q^+A^-$, $Q^+$ designating an ammonium, phosphonium and/or sulfonium cation, and $A^-$ designating an anion likely to form a liquid salt with said cation.

The composition and the availability conditions (temperature, pressure, amount) of the effluent to be treated thus depend on the location selected for extraction of the alcohol by the ionic liquid. These positions will be detailed precisely in the description in connection with FIG. 1. Treatment by an ionic liquid is located either on the ether-hydrocarbon-alcohol effluent at the outlet of the reaction section (stage b)), or on an effluent from the section of the fractionating column (stage c)).

The non-aqueous ionic liquid used in the present invention is selected from the group consisting of liquid salts having the general formula $Q^+$ $A^-$, wherein $Q^+$ designates an ammonium, phosphonium and/or sulfonium cation, and $A^-$ designates any anion, organic or inorganic, likely to form a liquid salt with said cation at low temperature, i.e. below 100° C., advantageously below 85° C. and preferably below 50° C.

In the non-aqueous ionic liquid of formula $Q^+A^-$, the $A^-$ anions are preferably selected from among are preferably selected from among the following anions: halogenides, nitrate, sulfate, alkylsulfates, phosphate, alkylphosphates, acetate, halogenoacetates, tetrafluoroborate, tetrachloroborate, hexafluorophosphate, trifluoro-tris-(pentafluoroethyl) phosphate, hexafluoroantimonate, fluorosulfonate, alkylsulfonates (methylsulfonate for example), perfluoroalkylsulfonates (trifluoromethylsulfonate for example), bis(perfluoroalkylsulfonyl)amidides (for example bis-trifluoromethane-sulfonyl amidide of formula $N(CF_3SO_2)_2^-$), tris-trifluoromethanesulfonyl methylide of formula $C(CF_3SO_2)_3^-$, arenesulfonates, possibly substituted by halogen or halogeno-alkyl groups, tetra(trifluoroacetoxy) borate, bis(oxalato)borate, dicyanamide, as well as the tetraphenylborate anions.

The $Q^+$ cations are preferably selected from among the group consisting of phosphonium, ammonium and/or sulfonium. In the formulas hereafter, $R^1$, $R^2$, $R^3$ and $R^4$ represent hydrogen, preferably a single substituent representing hydrogen (except for the $NH_4^+$ cation for $NR^1R^2R^3R^{4+}$), or hydrocarbyl radicals having 1 to 30 carbon atoms, for example alkyl groups, saturated or non-saturated, cycloalkyls or aromatics, aryls or aralkyls, possibly substituted, comprising 1 to 30 carbon atoms.

$R^1$, $R^2$, $R^3$ and $R^4$ can also represent hydrocarbyl radicals carrying one or more functions selected from among the following functions: —$CO_2R$, —$C(O)R$, —$OR$, —$C(O)NRR'$, —$C(O)N(R)NR'R''$, —$NRR'$, —$SR$, —$S(O)R$, —$S(O)_2R$, —$SO_3R$, —$CN$, —$N(R)P(O)R'R'$, —$PRR'$, —$P(O)RR'$, —$P(OR)(OR')$, —$P(O)(OR)(OR')$, wherein $R$, $R'$ and $R''$, identical or different, represent each hydrogen or hydrocarbyl radicals having 1 to 30 carbon atoms.

The ammonium and/or phosphonium $Q^+$ cations preferably meet one of the following general formulas: $[NR^1R^2R^3R^4]^+$ and $[PR^1R^2R^3R^4]^+$, or one of the general formulas: $[R^1R^2N=CR^3R^4]^+$ and $[R^1R^2P=CR^3R^4]^+$ wherein $R^1$, $R^2$, $R^3$ and $R^4$, identical or different, are defined as above.

The ammonium and/or phosphonium cations can also be derived from nitrogen-containing and/or phosphorus-containing heterocycles comprising 1, 2 or 3 nitrogen and/or phosphorus atoms, of general formulas:

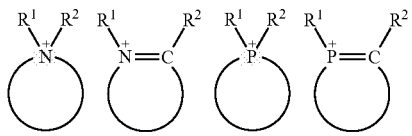

wherein the cycles consist of 4 to 10 atoms, preferably 5 to 6 atoms, and $R^1$ and $R^2$ are defined as above.

The ammonium or phosphonium cation can further meet one of the general formulas as follows:

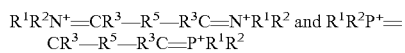

wherein $R^1$, $R^2$ and $R^3$, identical or different, are defined as above, and $R^5$ represents an alkylene or phenylene remainder.

Examples of $R^1$, $R^2$, $R^3$ and $R^4$ groups are the following radicals: methyl, ethyl, propyl, isopropyl, secondary butyl, tertiary butyl, butyl, amyl, phenyl or benzyl; $R^5$ can be a methylene, ethylene, propylene or phenylene group.

The ammonium and/or phosphonium $Q^+$ cation is preferably selected from among the group consisting of: N-butylpyridinium, N-ethylpyridinium, pyridinium, ethyl-3-methyl-1-imidazolium, butyl-3-methyl-1-imidazolium, hexyl-3-methyl-1-imidazolium, butyl-3-dimethyl-1,2-imidazolium, diethylpyrazolium, N-butyl-N-methylpyrrolidinium, trimethylphenylammonium, tetrabutylphosphonium and tributyltetradecyl-phosphonium.

The $Q^+$ sulfonium cations can have the general formula $[SR^1R^2R^3]^+$, where $R^1$, $R^2$ and $R^3$, identical or different, are defined as above.

Examples of salts that can be used in the method according to the invention are: N-butylpyridinium hexafluorophosphate, N-ethyl-pyridinium tetrafluoroborate, pyridinium fluorosulfonate, butyl-3-methyl-1-imidazolium tetrafluoroborate, butyl-3-methyl-1-imidazolium bis-trifluoromethane-sulfonyl)amidide, triethylsulfonium bis-trifluoromethane-sulfonyl amidide, butyl-3-methyl-1-imidazolium hexafluoro-antimonate, butyl-3-methyl-1-imidazolium hexafluorophosphate, butyl-3-methyl-1-imidazolium trifluoroacetate, butyl-3-methyl-1-imidazolium trifluoromethylsulfonate, butyl-3-methyl-1-imidazolium bis(trifluoromethylsulfonyl)amidide, triethylsulfonium bis-(trifluoromethylsulfonyl)amidide, trimethylphenylammonium hexafluorophosphate and tetrabutylphosphonium tetrafluoroborate. These salts can be used alone or in admixture.

The result of contacting the liquid effluent with the non-aqueous ionic liquid (solvent) used in the method according to the invention is selective absorption of the alcohol, insofar as the co-absorption, in the solvent, of the hydrocarbons whose chain has less than 10 carbon atoms is very low. In general, the alcohol/hydrocarbon molar ratio in the ionic liquid is above 150.

Ether co-absorption in the solvent is also low and the alcohol/ether molar ratio is above 10 and at least 5.

Contacting can be carried out by in-line mixing of the ionic liquid with the liquid effluent to be treated. Contacting can also be achieved in one or more liquid wash columns, for example in perforated tray type, valve tray type and/or bubble-cap tray type columns, or in random or stacked packing columns. It is also possible to use contactors, of static or dynamic type, for example a membrane contactor, wherein the liquid feed flows on one side of the membrane, the ionic liquid flowing on the other side of the membrane, and wherein mass exchanges occur through the membrane.

Stage e)

The stage of regenerating the non-aqueous ionic liquid used in the method according to the invention is carried out by separating in one or more separating drums and possibly by expanding the alcohol-laden ionic liquid in order to release species that may have been co-absorbed in said ionic liquid upon liquid-liquid contact, then by evaporating the alcohol. Alcohol evaporation is performed under temperature and pressure conditions adjusted by the person skilled in the art, which depend on economic considerations. In general, evaporation is carried out at a pressure ranging between 0.05 and 3.0 MPa, at the corresponding alcohol evaporation temperature.

After a condensation stage, the alcohol recovered is recycled to stage a) or to the fractionating column of stage c).

The water content of the recycled alcohol is markedly lower than the content that would be observed with water extraction (conventional system). This content is at most equal to 60% of the content of the prior art using a conventional system, and advantageously below 40% of the water content obtained with the conventional system.

The present invention is now described in connection with FIG. 1 that shows the various positions (I, II, III, IV, V and VI) for treatment of the alcohol-containing effluent by contact with an ionic liquid as described above. This treatment includes stage d) of extraction of the alcohol by the ionic liquid and ionic liquid regeneration stage e). FIG. 1 only shows the main equipments. This figure describes several embodiments of the invention by way of non limitative example.

The hydrocarbon fraction containing iso-olefins is conveyed through line (1) prior to being mixed with an outer source of alcohol supplied through line (2) and with the recycled alcohol fraction supplied through line (26). The mixture is then fed into reaction section (4) through line (3). The effluent leaving the reaction section through line (5) comprises a mixture of unreacted or unreactive hydrocarbons, of ether (reaction product) and of unreacted alcohol. In general, this effluent is made up of 10 to 60% ether, 1 to 10% alcohol and 30 to 80% hydrocarbons (molar ratios), its pressure ranging between 0.8 and 2 MPa and its temperature between 50° C. and 90° C. It can optionally enter a zone for treatment through contact with an ionic liquid (zone (I) in FIG. 1) as described above.

If such a zone is present, the alcohol extracted from said ionic liquid by evaporation (not shown) is recycled after condensation to reaction section (4) through lines (6), (13) and (26).

After expansion through a valve ($V_{57}$), the effluent to be treated optionally passes into a zone (II) for contacting with an ionic liquid. The effluent circulating in line (7) is generally at a pressure ranging between 0.2 and 1.5 MPa. The pressure depends on the ether produced and/or on the hydrocarbon cut treated. For the production of MTBE and ETBE, this pressure ranges between 0.5 and 1.5 MPa, preferably between 0.7 and 1 MPa. For the production of TAME or ETAE, which are heavier ethers, this pressure ranges between 0.2 and 1.5 MPa, preferably between 0.2 and 0.5 MPa.

The temperature of said effluent ranges between 50° C. and 90° C. The alcohol extracted by the ionic liquid is recycled to reaction section (4) through lines (8), (13) and (26).

At the outlet of zone (II) or of line (7), the liquid effluent flows through a line (9) into a heat exchanger (E1) so as to be heated and brought to a temperature generally ranging between 80° C. and 100° C.

At the outlet of this exchanger, a line (10) carries the effluent to an optional zone for treatment through contact with an ionic liquid (zone (III) in FIG. 1). If such a zone is present, the alcohol extracted by the ionic liquid is recycled to reaction section (4) through lines (12), (13) and (26).

Preferably, a single zone among zones (I), (II) and (III) of FIG. 1 is present, but it is not impossible that several are present.

When alcohol recovery has already been carried out in a zone (I), (II) or (III), the ether-hydrocarbon-alcohol (alcohol present as traces) liquid effluent then flows into column (14) in order to separate the ether fraction from the hydrocarbon-ether fraction. In the latter case, column (14) cannot be a catalytic column because the alcohol has been extracted.

If alcohol recovery has not been carried out in a zone (I), (II) or (III), the ether-hydrocarbon-alcohol liquid effluent also flows into a column (14)—catalytic or not—allowing separation of the (more or less alcohol-rich) ether fraction from a hydrocarbon-alcohol fraction generally freed of almost all of the ether.

At the top of column (14), a line (15) carries a hydrocarbon-alcohol gaseous mixture to an exchanger (E2) and then to a reflux drum (16) allowing to recover the condensed vapours through line (18) and to discharge the gas fraction through line (17). Reflux pump (P1) allows both to provide reflux to column (14) through line (19) and to supply through line (20) an optional zone for treatment through contact with an ionic liquid, zone (V) in FIG. 1. The molar composition of the hydrocarbon-alcohol fraction generally ranges between 90 and 98% hydrocarbons and 1 to 98% alcohol. The temperature ranges between 25° C. and 60° C. and the pressure ranges between 0.2 and 1.5 MPa. At the outlet of zone (V), line (21) allows the extracted alcohol to be recycled to reaction zone (4) through line (26). If the alcohol has been entirely extracted in zones (I), (II) and/or (III), zone (V) is normally not necessary.

The mixture at the bottom of column (14) is discharged through line (22) and generally sent, after passage through an exchanger (E3), to an optional zone for treatment through contact with an ionic liquid (zone (IV) in FIG. 1). The composition of the ether-alcohol mixture at the bottom of column (14) generally ranges between 0.5 and 15% (by mole) alcohol and it contains less than 1000 ppm by weight of hydrocarbons. The temperature ranges between 25° C. and 60° C., and the pressure ranges between 0.2 and 1.5 MPa. At the outlet of zone (IV), line (23) allows the alcohol extracted to be recycled to separation column (14).

At the level of column (14), lateral withdrawal in the exhausting section of the column can also be carried out through a line (24) that carries, generally after passage through an exchanger (E4), an ether-hydrocarbon-alcohol mixture containing less than 1% by mole of hydrocarbons to an optional zone for treatment through contact with an ionic liquid (zone (VI) in FIG. 1). The ether-hydrocarbon-alcohol mixture at the inlet of zone (VI) predominantly contains ether, generally 0.5 to 1% by mole of hydrocarbons and 0.5 to 15% by mole of alcohol. The temperature ranges between 25° C. and 60° C. and the pressure ranges between 0.2 and 1.5 MPa. At the outlet of zone (VI), line (25) allows the extracted alcohol to be recycled preferably to a tray of column (14) located above the draw-off pan, which globally allows the alcohol in question to get to the top of column (14) under the influence of the various azeotropes that form in this column.

Position V is the preferred position among the six positions I, II, III, IV, V and VI in FIG. 1.

Figure 2:
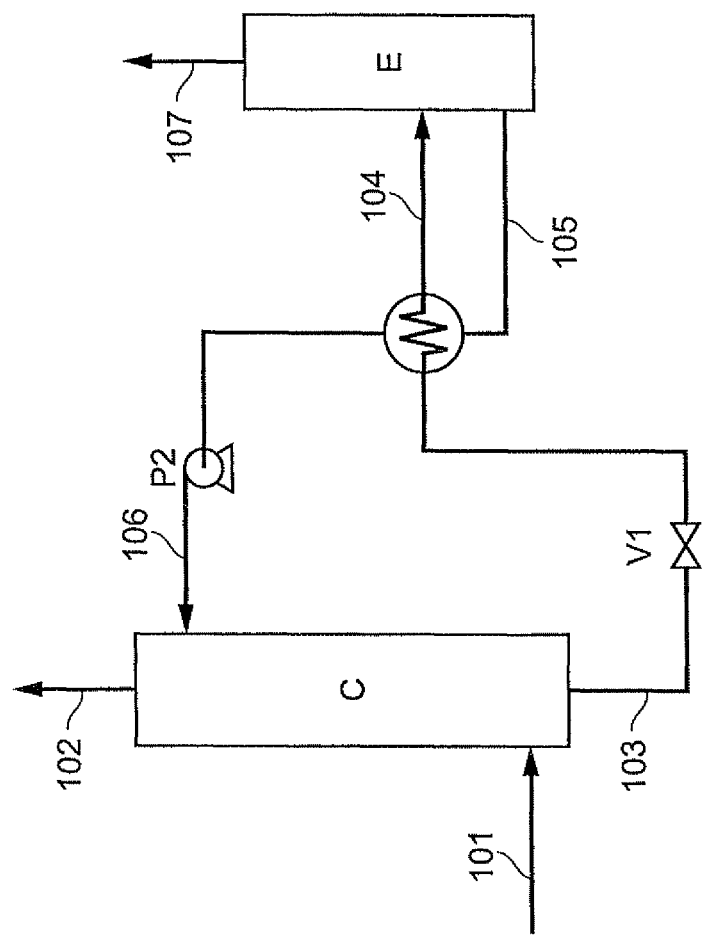

FIG. 2 describes the operating principle of the zone intended for treatment through contact with an ionic liquid. The principle is the same for each position (I) to (VI).

The effluent to be treated flows through line (101) into contacting zone (C) where it is contacted with the ionic liquid. The alcohol-laden ionic liquid is discharged from zone (C) through a line (103) while the alcohol-depleted liquid effluent is discharged through line (102). The ionic liquid circulating in line (103) can be expanded through valve ($V_1$), possibly fed into a separating drum (not shown in FIG. 2), then it can be heated in a heat exchanger. It is thereafter sent through line (104) into evaporation zone (E). The evaporated alcohol is discharged through line (107) at the evaporator top and it is condensed downstream whereas the regenerated ionic liquid is carried by line (105) under the action of pump P2 that sends it to contacting zone (C) through line (106).

The advantages of the present invention will be clear from reading the examples hereafter.

EXAMPLES

Example 1

Comparative

Starting from the basic scheme of an ETBE production unit, a C4 hydrocarbon-containing water-saturated feed comprising 16.7% by mole of isobutene is introduced into a first etherification reactor at a flow rate of 580 kmol/h with an ethanol feed at a molar flow rate of 113 kmol/h containing 0.4% water. The stream leaving the first reactor is divided into two effluents, the first one representing 60% of the stream is recycled to the first reactor so as to optimize the iso-olefin conversion ratio. The second one is distilled in a catalytic column so as to obtain, at the top, an ethanol-rich hydrocarbon cut and, at the bottom of the column, the alcohol-free ether (ETBE).

15 kmol/h ethanol are recovered with 2.5 kmol/h water by washing the hydrocarbon cut with water, then by distilling in order to separate the water from the alcohol as described in the prior art. The washing operation first consists in contacting, in a 30-tray column operating at 0.8 MPa and 45° C., the 513 kmol/h ethanol-laden hydrocarbons obtained at the top of the distillation column with 80 kmol/h water. A water-ethanol mixture containing 15.5% by mole of alcohol is obtained. This effluent is then sent to a distillation column comprising 30 trays and operating at 130° C. and 0.26 MPa in the bottom of the column. The alcohol extracted during this distillation, which still contains 14% by mole of water, is then recycled to the reaction section.

Example 2

According to the Invention

The reactant implementation conditions described in Example 1 are repeated and a stage of contacting the liquid effluent with 1-butyl-3-methylimidazolium trifluoroacetate is positioned at the top of the separation column (position V of FIG. 1). An alcohol whose purity is above 99% and containing less than 1% by mole of water is thus recycled to the reaction section. Extraction of the alcohol requires using 30 kmol/h ionic liquid, in a column with two theoretical stages operating at 0.8 MPa and 45° C. Regeneration of the ionic liquid is carried out in a simple evaporator. Recycling this water-poor alcohol thus allows to obtain a 0.2% gain as regards the isobutene conversion efficiency, and the ETBE selectivity is markedly higher since the tert-butyl alcohol (TBA) content is decreased by at least 50% in comparison with the use of an alcohol recovered according to the conventional technology described in Example 1.

The invention claimed is:

1. A method of producing ethers from iso-olefins and ethanol, consisting of the following stages:
    a) mixing a hydrocarbon fraction containing iso-olefins with at least one alcohol stream that contains ethanol,
    b) etherification reaction by reaction of the mixture obtained in stage a) in the presence of an ion-exchange resin so as to obtain an ether-hydrocarbon-alcohol effluent,
    c) separation, in a fractionating column, of said ether-hydrocarbon-alcohol effluent into a first ether-enriched effluent containing part of the excess alcohol and into a second hydrocarbon-enriched effluent containing the other part of the excess alcohol,
and treating the second hydrocarbon-enriched effluent obtained in stage c) by carrying out the following stages:
    d) contacting said effluent with a non-aqueous ionic liquid so that the ionic liquid becomes laden with alcohol and the effluent becomes depleted in alcohol, the ionic liquid having the formula $Q^+ A^-$, $Q^+$ designating an ammonium, phosphonium and/or sulfonium cation, and $A^-$ designating an anion likely to form a liquid salt with said cation,
    e) regenerating the alcohol-laden ionic liquid by separating said ionic liquid and the alcohol, said separation consisting in evaporating the alcohol, and then condensing it, and wherein said separated and condensed alcohol is recycled in the process to stage a).

2. A method of producing ethers from iso-olefins and ethanol, consisting of the following stages:
    a) mixing a hydrocarbon fraction containing iso-olefins with at least one alcohol stream that contains ethanol,
    b) etherification reaction by reaction of the mixture obtained in stage a) in the presence of an ion-exchange resin so as to obtain an ether-hydrocarbon-alcohol effluent,
    c) separation, in a fractionating column, of said ether-hydrocarbon-alcohol effluent into a first ether-enriched effluent containing part of the excess alcohol and into a second hydrocarbon-enrich effluent containing the other part of the excess alcohol,
and treating the second hydrocarbon-enriched effluent obtained in stage c) by carrying out the following stages:
    d) contacting said effluent with a non-aqueous ionic liquid so that the ionic liquid becomes laden with alcohol and the effluent becomes depleted in alcohol, the ionic liquid having the formula $Q^+ A^-$, $Q^+$ designating an ammonium, phosphonium and/or sulfonium cation, and $A^-$ designating an anion likely to form a liquid salt with said cation,
    e) regenerating the alcohol-laden ionic liquid by separating said ionic liquid and the alcohol, said separation consisting in evaporating the alcohol, and then condensing it,
and wherein said separated and condensed alcohol is recycled in the process to stage a). and wherein one of I) to IX) apply
    I) the effluent from stage b), made up of 30 to 80% by mole of hydrocarbons, 10 to 60% by mole of ether and 1 to 10% by mole of alcohol, is additionally treated according to stage d) at a pressure ranging between 0.8 and 2 MPa and at a temperature ranging between 50° C. and 90° C., so as to obtain at the end of stage e) an alcohol that is recycled to stage a);
    II) the effluent from stage b), made up of 30 to 80% by mole of hydrocarbons, 10 to 60% by mole of ether and 1 to 10% by mole of alcohol, is additionally expanded and treated according to stage d) at a pressure ranging between 0.2 and 1.5 MPa and at a temperature ranging between 50° C. and 90° C., so as to obtain at the end of stage e) an alcohol that is recycled to stage a);
    III) the effluent from stage b), made up of 30 to 80% by mole of hydrocarbons, 10 to 60% by mole of ether and 1 to 10% by mole of alcohol, is additionally heated and treated according to stage d) at a pressure ranging between 0.2 and 1.5 MPa and at a temperature ranging between 80° C. and 100° C., so as to obtain at the end of stage e) an alcohol that is recycled to stage a);
    IV) the second effluent from stage c), made up of 90 to 98% by mole of hydrocarbons and of 1 to 98% by mole of alcohol, is treated according to stage d) at a pressure ranging between 0.2 and 1.5 MPa and at a temperature ranging between 25° C. and 6020 C., so as to obtain at the end of stage e) an alcohol that is recycled to stage a);
    V) the first effluent from stage c), enriched in ether and containing 0.5 to 15% by mole of alcohol and less than 1000 ppm by weight of hydrocarbons, is treated according to stage d) at a pressure ranging between 0.2 and 1.5 MPa and at a temperature ranging between 25° C. and 60° C., so as to obtain at the end of stage e) an alcohol that is recycled to the fractionating column of stage c);
    VI) the first effluent from stage c), enriched in ether and containing 0.5 to 15% by mole of alcohol and 0.5 to 1% by mole of hydrocarbons, is treated according to stage d) at a pressure ranging between 0.2 and 1.5 MPa and at a temperature ranging between 25° C. and 60° C., so as to obtain at the end of stage e) an alcohol that is recycled to the fractionating column of stage c);

VII) additionally treating in stages d) and e) the first ether-enriched effluent containing part of the excess alcohol from stage c);

VIII) additionally recycling to stage c) separated and condensed alcohol;

IX) additionally treating the effluent obtained in stage b) by carrying out the following stages:

a) contacting said effluent with a non-aqueous ionic liquid so that the ionic liquid becomes laden with alcohol and the effluent becomes depleted in alcohol, the ionic liquid having the formula $Q^+ A^-$, $Q^+$ designating an ammonium, phosphonium and/or sulfonium cation, and $A^-$ designating an anion likely to form a liquid salt with said cation, b) regenerating the alcohol-laden ionic liquid by separating said ionic liquid and the alcohol, said separation consisting in evaporating the alcohol, and then condensing it, and wherein said separated and condensed alcohol is recycled in the process to stage a).

3. A method as claimed in claim 1, wherein the effluent from stage b), made up of 30 to 80% by mole of hydrocarbons, 10 to 60% by mole of ether and 1 to 10% by mole of alcohol, is additionally treated according to stage d) at a pressure ranging between 0.8 and 2 MPa and at a temperature ranging between 50° C. and 90° C., so as to obtain at the end of stage e) an alcohol that is recycled to stage a).

4. A method as claimed in claim 1, wherein the effluent from stage b), made up of 30 to 80% by mole of hydrocarbons, 10 to 60% by mole of ether and 1 to 10% by mole of alcohol, is additionally expanded and treated according to stage d) at a pressure ranging between 0.2 and 1.5 MPa and at a temperature ranging between 50° C. and 90° C., so as to obtain at the end of stage e) an alcohol that is recycled to stage a).

5. A method as claimed in claim 1, wherein the effluent from stage b), made up of 30 to 80% by mole of hydrocarbons, 10 to 60% by mole of ether and 1 to 10% by mole of alcohol, is additionally heated and treated according to stage d) at a pressure ranging between 0.2 and 1.5 MPa and at a temperature ranging between 80° C. and 100° C., so as to obtain at the end of stage e) an alcohol that is recycled to stage a).

6. A method as claimed in claim 1, wherein the second effluent from stage c), made up of 90 to 98% by mole of hydrocarbons and of 1 to 98% by mole of alcohol, is treated according to stage d) at a pressure ranging between 0.2 and 1.5 MPa and at a temperature ranging between 25° C. and 60° C., so as to obtain at the end of stage e) an alcohol that is recycled to stage a).

7. A method as claimed in claim 1, wherein the first effluent from stage c), enriched in ether and containing 0.5 to 15% by mole of alcohol and less than 1000 ppm by weight of hydrocarbons, is treated according to stage d) at a pressure ranging between 0.2 and 1.5 MPa and at a temperature ranging between 25° C. and 60° C., so as to obtain at the end of stage e) an alcohol that is recycled to the fractionating column of stage c).

8. A method as claimed in claim 1, wherein the first effluent from stage c), enriched in ether and containing 0.5 to 15% by mole of alcohol and 0.5 to 1% by mole of hydrocarbons, is treated according to stage d) at a pressure ranging between 0.2 and 1.5 MPa and at a temperature ranging between 25° C. and 60° C., so as to obtain at the end of stage e) an alcohol that is recycled to the fractionating column of stage c).

9. A method as claimed in claim 1, wherein the $A^-$ anion is selected from the group consisting of halogenides, nitrate, sulfate, alkylsulfates, phosphate, alkylphosphates, acetate, halogenoacetates, tetrafluoroborate, tetrachloro-borate, hexafluorophosphate, trifluoro-tris-(pentafluoroethyl)phosphate, hexafluoro-antimonate, fluorosulfonate, alkylsulfonates, perfluoroalkylsulfonates, bis(perfluoro-alkylsulfonyl)amidides, tris-trifluoromethanesulfonyl methylide of formula $C(CF_3SO_2)_3^{31}$, arenesulfonates, tetra(trifluoroacetoxy)borate, bis(oxalato)borate, dicyanamide and tetraphenylborate anions.

10. A method as claimed in claim 1, wherein the $Q^+$ cation is of formula $[NR^1R^2R^3R^4]^+$, $[PR^1R^2R^3R^4]^+$, $[R^1R^2N=CR^3R^4]^+$ or $[R^1R^2P=CR^3R^4]^+$ wherein $R^1$, $R^2$, $R^3$ and $R^4$, identical or different, represent hydrogen or a hydrocarbyl having 1 to 30 carbon atoms.

11. A method as claimed in claim 1, wherein the $Q^{30}$ cation has been derived from nitrogen-containing and/or phosphorus-containing heterocycles comprising 1, 2 or 3 nitrogen and/or phosphorus atoms, the heterocycle containing 4 to 10 carbon atoms.

12. A method as claimed in claim 1, wherein the $Q^+$ cation has one of the general formulas

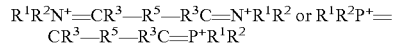

wherein $R^1$, $R^2$ and $R^3$, identical or different, represent hydrogen or a hydrocarbyl having 1 to 30 carbon atoms, and $R^5$ represents an alkylene or phenylene remainder residue.

13. A method as claimed in claim 1, wherein the $Q^+$ cation is any of N-butylpyridinium, N-ethylpyridinium, pyridinium, ethyl-3-methyl-1-imidazolium, butyl-3-methyl-1-imidazolium, hexyl-3-methyl-1-imidazolium, butyl-3-dimethyl-1,2-imidazolium, diethylpyrazolium, N-butyl-N-methylpyrrolidinium, trimethylphenylammonium, tetrabutylphosphonium and tributyl-tetradecyl-phosphonium.

14. A method as claimed in claim 1, wherein the $Q^+$ cation has the general formula $[SR^1R^2R^3]^+$, where $R^1$, $^2$ and $R^3$, identical or different, represent hydrogen or a hydrocarbyl having 1 to 30 carbon atoms.

15. A method as claimed in claim 1, wherein the non-aqueous ionic liquid is any of N-butylpyridinium hexafluorophosphate, N-ethyl-pyridinium tetrafluoroborate, pyridinium fluorosulfonate, butyl-3-methyl-1-imidazolium tetrafluoroborate, butyl-3-methyl-1-imidazolium bis-trifluoromethane-sulfonyl)amidide, triethylsulfonium bis-trifluoromethane-sulfonyl amidide, butyl-3-methyl-1-imidazolium hexafluoro-antimonate, butyl--3-methyl-1-imidazolium hexafluoro-phosphate, butyl-3-methyl-1-imidazolium trifluoroacetate, butyl-3-methyl-1-imidazolium trifluoromethylsulfonate, butyl-3-methyl-1-imidazolium bis(trifluoro-methylsulfonyl)amidide, triethylsulfonium bis-(trifluoromethylsulfonyl)amidide, trimethylphenylammonium hexafluorophosphate and tetrabutylphosphonium tetrafluoroborate.

16. A method according to claim 1, wherein $A^-$ is combinable with said cation to form a liquid salt at a temperature less than 100° C.

17. A method as claimed in claim 1, which additionally includes treating in stages d) and e) the first ether-enriched effluent containing part of the excess alcohol from stage c).

18. A method as claimed in claim 1, which additionally includes recycling to stage c) separated and condensed alcohol.

19. A method as claimed in claim 1, which additionally includes treating the effluent obtained in stage b) by carrying out the following stages:
- a) contacting said effluent with a non-aqueous ionic liquid so that the ionic liquid becomes laden with alcohol and the effluent becomes depleted in alcohol, the ionic liquid having the formula $Q^+ A^-$, $Q^+$ designating an ammonium, phosphonium and/or sulfonium cation, and $A^-$ designating an anion likely to form a liquid salt with said cation,
- b) regenerating the alcohol-laden ionic liquid by separating said ionic liquid and the alcohol, said separation consisting in evaporating the alcohol, and then condensing it, and wherein said separated and condensed alcohol is recycled in the process to stage a).

20. A method as claimed in claim 1, wherein the non-aqueous ionic liquid is N-butylpyridinium hexafluorophosphate, N-ethyl-pyridinium tetrafluoroborate, pyridinium fluorosulfonate, butyl -3-methyl-1-imidazolium tetrafluoroborate, butyl-3-methyl-1-imidazolium bis-trifluoromethane-sulfonyl) amidide, triethylsulfonium bis-trifluoromethane-sulfonyl amidide, butyl-3-methyl-1-imidazolium hexafluoro-antimonate, butyl-3-methyl-1-imidazolium hexafluoro-phosphate, butyl-3-methyl-1-imidazolium trifluoroacetate, butyl-3-methyl-1-imidazolium trifluoromethylsulfonate, butyl-3-methyl-1-imidazolium bis(trifluoro-methylsulfonyl)amidide, triethylsulfonium bis-(trifluoromethylsulfonyl)amidide, trimethylphenylammonium hexafluorophosphate or tetrabutylphosphonium tetrafluoroborate.

* * * * *

UNITED STATES PATENT AND TRADEMARK OFFICE
CERTIFICATE OF CORRECTION

PATENT NO.      : 8,748,671 B2  
APPLICATION NO. : 12/300007  
DATED           : June 10, 2014  
INVENTOR(S)     : Forestiere et al.

It is certified that error appears in the above-identified patent and that said Letters Patent is hereby corrected as shown below:

In the Claims

Column 10, line 55 reads "ranging between 25°C. and 60$20$ C., so as to obtain at" should read
-- ranging between 25 °C. and 60 °C., so as to obtain at --

Column 12, line 11 reads "formula $C(CF_3SO_2)_3{}^{31}$, arenesulfonates, tetra(trifluoroac-" should read
-- formula $C(CF_3SO_2)_3{-}$, arenesulfonates, tetra(trifluoroac- --

Column 12, line 19 reads "11. A method as claimed in claim 1, wherein the $Q^{30}$ cation" should read
-- 11. A method as claimed in claim 1, wherein the $Q^+$ cation --

Signed and Sealed this  
First Day of September, 2015

Michelle K. Lee  
*Director of the United States Patent and Trademark Office*